US00PP19929P3

(12) United States Plant Patent
Bautista

(10) Patent No.: US PP19,929 P3
(45) Date of Patent: Apr. 21, 2009

(54) ***HELICHRYSUM* PLANT NAMED 'RASPBERRY'**

(50) Latin Name: ***Helichrysum bracteatum* ×*splendum***
Varietal Denomination: Raspberry

(75) Inventor: Rodolfo Valdoz Bautista, Half Moon Bay, CA (US)

(73) Assignee: Bay City Flower Company, Half Moon Bay, CA (US)

( * ) Notice: Subject to any disclaimer, the term of this patent is extended or adjusted under 35 U.S.C. 154(b) by 0 days.

(21) Appl. No.: 11/496,875

(22) Filed: Jul. 31, 2006

(65) Prior Publication Data

US 2008/0184418 P1 Jul. 31, 2008

(51) Int. Cl.
*A01H 5/00* (2006.01)

(52) U.S. Cl. ..... Plt./359

(58) Field of Classification Search ..... Plt./359
See application file for complete search history.

*Primary Examiner*—Annette H Para
*Assistant Examiner*—S. B McCormick Ewoldt
(74) *Attorney, Agent, or Firm*—James R. Cypher; Charles R. Cypher

(57) ABSTRACT

A plant variety of the *Helichrysum* family resulting from a controlled crossing of the varieties of *Helichrysum bracteatum bracteatum×splendidum* 'Harvest Plum' the subject of U.S. Plant Pat. No. 10,742 and *Helichrysum bracteatum× splendidum* 'Lemon'. The new variety named 'Raspberry' has blooms of R.H.S. 59 C (red-purple groups. The new variety has an erect but compact growth habit, and can be easily forced in pots.

4 Drawing Sheets

Botanical classification: *Helichrysum bracteatum×splendidum.*
Variety denomination: 'Raspberry'.

BACKGROUND OF THE INVENTION

The present invention relates to a new and distinct variety of the Compositae family. The new variety is named *Helichrysum bracteatum×splendidum* 'Raspberry'.

This new *Helichrysum* variety originated as a seedling. It was selected from the progeny of a controlled hybridization conducted by the inventor in a commercial nursery in the city of Half Moon Bay. Half Moon Bay is located in San Mateo County, in the state of California.

The inventor crossed *Helichrysum bracteatum bracteatum×splendidum* 'Harvest Plum' the subject of U.S. Plant Pat. No. 10,742 and the unpatented (but currently pending) *Helichrysum bracteatum×splendidum* 'Lemon' to produce the new variety, *Helichrysum bracteatum bracteatum×splendidum* 'Harvest Plum' was the seed parent. The new variety was selected for commercial development because of its unique flower head color and compact growth habit. The new variety is particularly suitable for commercial plant culture because of its long-lasting flowers and attractive coloring.

Other desirable characteristics of the new variety are: the color of its flower head and bud, its dense foliage and strong stems, its compact growth habit, and its ability to grow well in pots in which it can be sold.

The infloresence is made up of a number of involucral bracts, surrounding a disk head. The bracts are striated with non-pigmented portions. Generally, the base of the bracts is not pigmented. The pigmentation pattern is the same for both the abaxial and the adaxial sides of the bracts. The outermost involucral bracts of the bud appear as R.H.S. 62 B (red-purple group). The rest of the bracts have an overall appearance of R.H.S. 58 D (red-purple group). The margins and tips of the upper bracts is R.H.S. 59 C (red-purple group).

The following table compares the new variety to the closest varieties known to the inventor, according to the new variety's distinguishing characteristics. The variety designated '1A93' is a progeny of a cross between *Helichrysum splendidum* (Thunb.) Less. and *Helichrysum bracteatum* (Venten.) Andr. The variety designated 'Harvest Sun' is the progeny of a cross between the variety designated '1A93' and *Helichrysum bracteatum* (Vent.). Andr.

TABLE 1

| | *H. bracteatum* (general characteristics) | *H. splendidum* | '1A93' | 'Harvest Sun' |
|---|---|---|---|---|
| Bract color | Various colors | Involucral bracts at opening are predominantly R.H.S. 12A. Upper involucral bracts when flower head is mature are predominantly R.H.S. 12A. | R.H.S. 4A | Involucral bracts at opening are predominantly R.H.S. 22A. Upper involucral bracts when flower head is mature are predominantly R.H.S. 9A. |
| Bud color | Various colors | Predominantly R.H.S. 175A. | R.H.S. 187B | R.H.S. 26A |
| Leaf surfaces | Puberulent | Tomentose | puberulent and | puberulent and |

TABLE 1-continued

| | | | | |
|---|---|---|---|---|
| | | | sparsely villous, main veins are hirsute | sparsely villous, main veins are hirsute |
| Suitability for pot culture | Good | Average | Good | Good |
| Ease of forcing | Generally good | Difficult | Good | Good |
| Growth habit | Generally compact | Spreading | Compact | Compact |

| | | 'Harvest Plum' | 'Harvest Lemon' | New Variety |
|---|---|---|---|---|
| | Bract color | Bract tips: R.H.S. 66D. Bract base: R.H.S. 155C. (Tip color dominates in all but innermost bracts.) | R.H.S 5 B | R.H.S 58 D |
| | Bud color | Bract tips: R.H.S. 187A. Bract base: R.H.S. 67B | R.H.S. 160 D (greyed-yellow group) | R.H.S. 187 D (greyed-purple group) |
| | Leaf surfaces | puberulent | Puberulent | puberulent |
| | Suitability for pot culture | Good | Good | Good |
| | Ease of forcing | Good | Good | Good |
| | Growth habit | Compact | Compact | Compact |

The distinguishing characteristics are retained by asexually reproduced, successive generations. The inventor, at a commercial nursery in Half Moon Bay, Calif., has asexually reproduced the new variety through three successive generations by means of cuttings and has found that the combination of characteristics as herein disclosed remain firmly fixed.

BRIEF DESCRIPTION OF THE DRAWINGS

The accompanying drawings consist of color photographs that show the typical potted-plant form, including the inflorescence, foliage, and bract color development from the bud stage to the mature flower head. The colors are represented as truly as possible using conventional photographic procedures.

DETAILED DESCRIPTION OF THE NEW VARIETY

Figure 1:
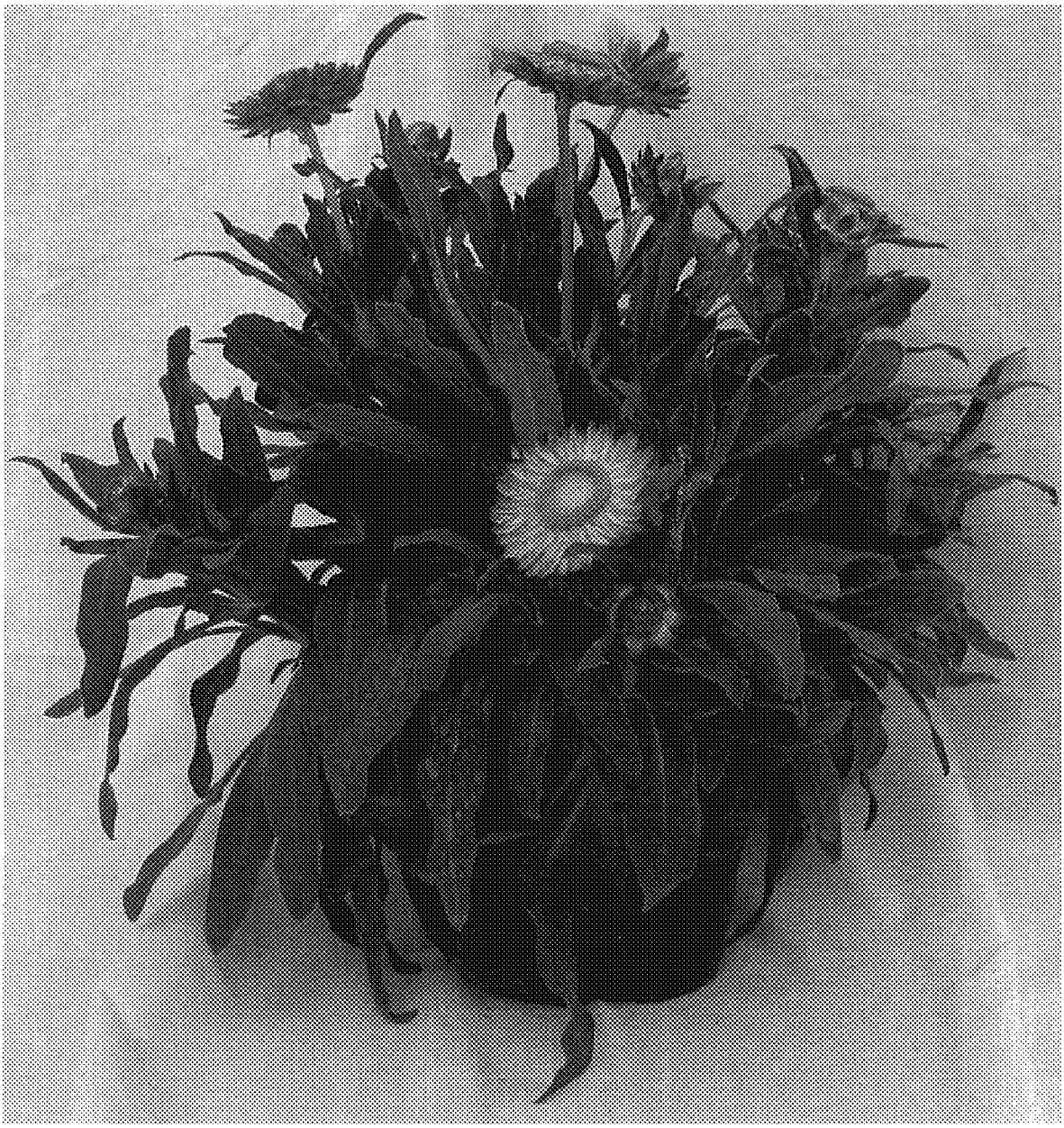
FIG. 1 is a perspective view of a potted plant of the new variety described herein, illustrating the overall form and appearance of the plant in full bloom.
Figure 2:
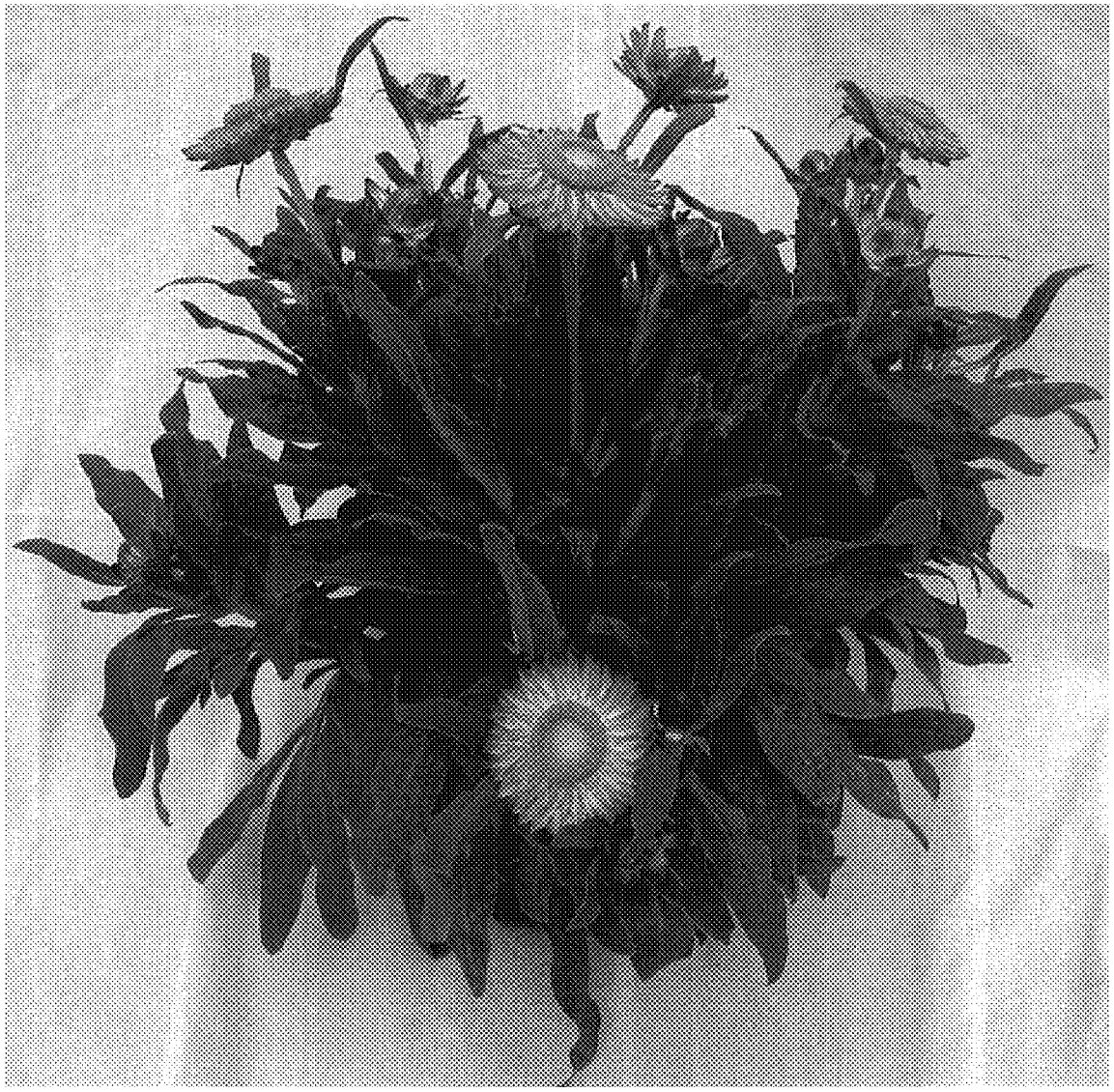
FIG. 2 is a top view of a potted plant of the new variety described herein, illustrating the overall form and appearance of the plant in full bloom.
Figure 3:
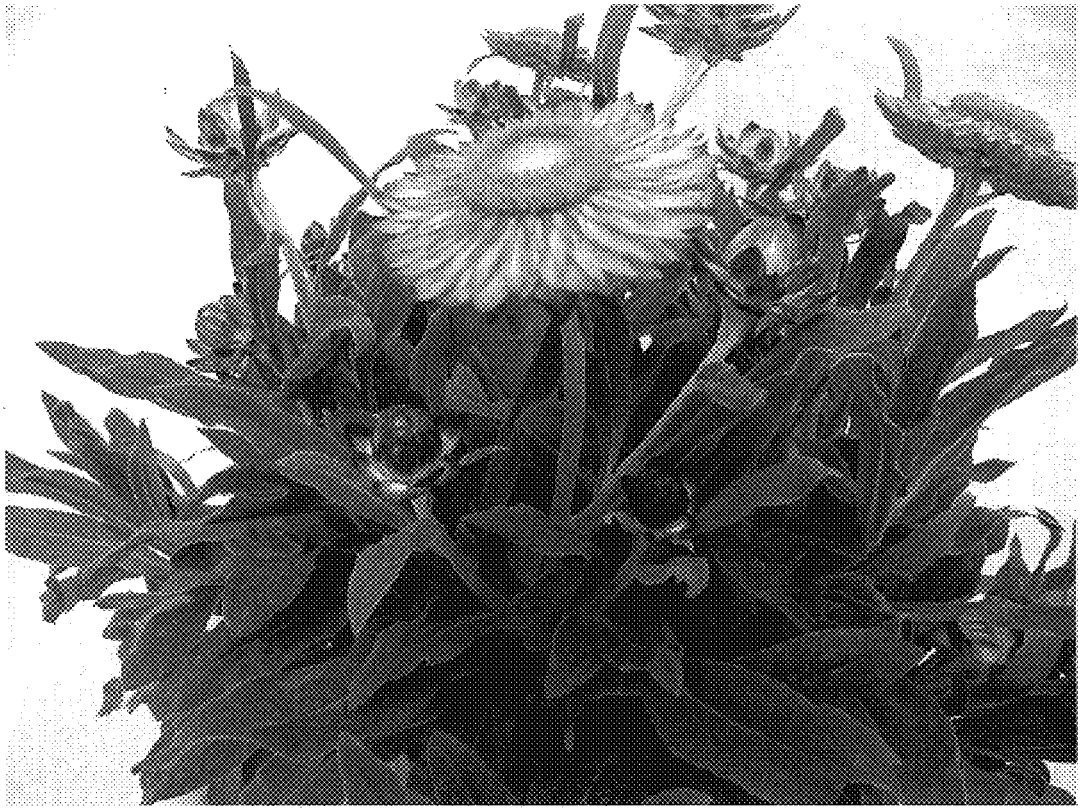
FIG. 3 is view of a potted plant of the new variety described herein, illustrating the overall form and appearance of the plant in full bloom.
Figure 4:
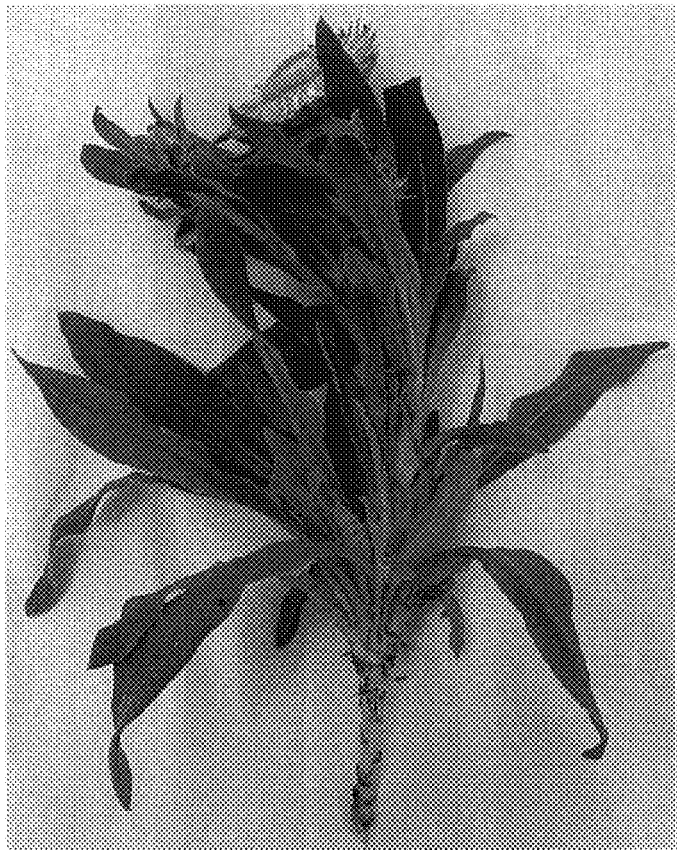
FIG. 4 is a view of one stem removed from the plant.
Figure 5:
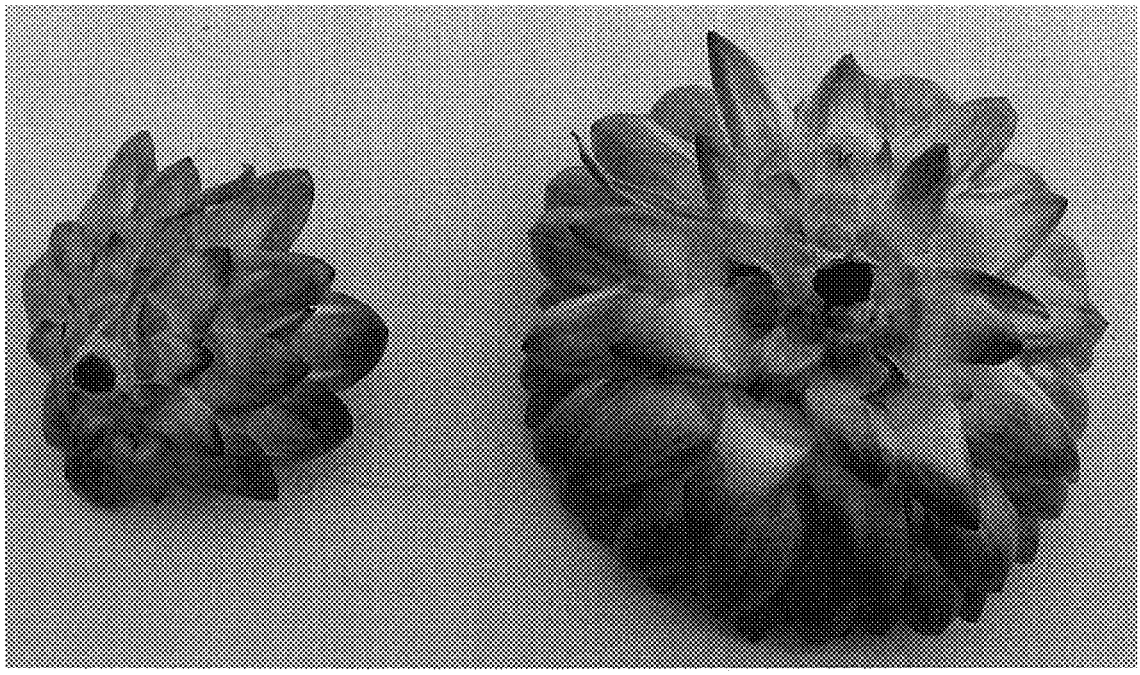
FIG. 5 is a view of the underside of two individual flower heads of the new variety described herein, showing the pigmentation pattern of the bracts.
Figure 6:
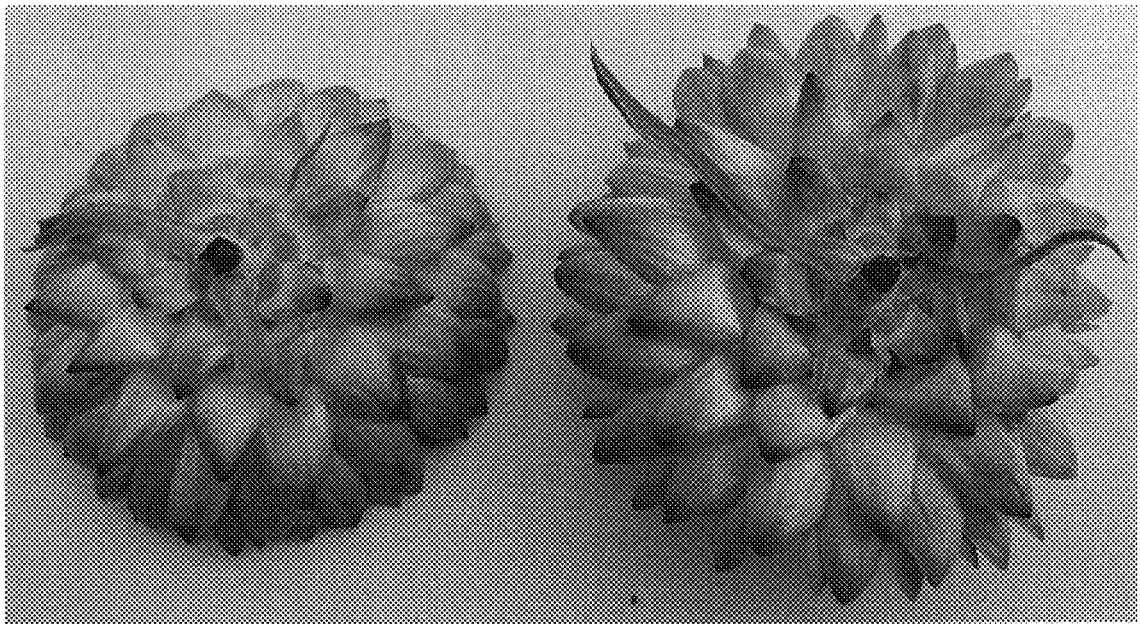
FIG. 6 is a view of the underside of two individual flower heads of the new variety described herein, showing the pigmentation pattern of the bracts.

The following is a detailed description of the new variety. The new variety has not been observed under all possible environmental conditions. Color designation and other values stated may deviate slightly from the stated values from flowering to flowering, but the deviations will be within the range expected from varying environmental, seasonal and cultural conditions. Color designations were made according to the R.H.S. Colour Chart published by The Royal Horticultural Society of London, England.

The following description is based on observations of optimally fertilized plants grown outside in 6 inch pots.

Cuttings were taken from mature plants in the summer and placed in cells. Plants were transplanted to 6" pots approximately 4 to 6 weeks after root initiation occurred.

The observed plants were 20 weeks old.

The plants were grown under glass in Half Moon Bay, Calif., during the winter and spring months. The day time temperature in the green house where the plants were grown was kept between 65 and 73 degrees Fahrenheit during the day and 65 degrees Fahrenheit at night. The humidity was maintained at 90%.

The plant:

*Name.*—*Helichrysum bracteatum×splendidum* 'Raspberry'.

*Origin.*—Seedling.

*Parentage.*—*Helichrysum bracteatum×splendidum* 'Harvest Plum' and *Helichrysum bracteatum×splendidum* 'Lemon', *Helichrysum bracteatum bracteatum×splendidum* 'Harvest Plum' was the seed parent.

*Classification.*—Family — Compositae. Tribe. — Inula. Genus. — *Helichrysum*. Species. —*Helichrysum bracteatum×splendidum*. Commercial. — Strawflower.

*Form.*—Upright, compact, biennial herb.

*Height.*—Plant grown in 6" pot is 29 cm.

*Diameter.*—Plant grown in 6" pot is 33 cm.

*Growth.*—Upright, vigorous growth under glass with excellent branching; easily forced to bloom without growth regulators.

*Stems.*—Texture. — Generally, stems are moderately pubescent at their base; stems are very sericeous below the flower, making for a glaucous appearance. Shape. — Stems have a rectangular cross section below the base of the flower becoming round at base. Size. — Stem width at top of plant below the terminal flower head is 5 mm. The stem widens in one direction to accommodate axilary stems, becoming approximately 10 mm wide. Where stems meet the original cutting, the stems are approximately 8 mm to 11 mm wide. The diameter of the original cutting is 15 mm.

*Foliage.*—Quantity. — Abundant. Shape. — Linear, narrowly acute; margins are repand; pinnately veined. Size. — As large as 16 cm long by 37 mm wide. Texture. — Viscid; main vein dominates on the underside of leaf and is sunken on the leaf surface. Pubescence. — Leaf surfaces are puberulent. Color.

— Upper leaf surface is R.H.S. 137A to 137 B (green group); lower leaf surface is R.H.S. 137C (green group).

*Disease resistance.*—Roots appear to be disease resistant.

The Bud:

*Form.*—Conical, with imbricate involucral bracts.

*Texture.*—Smooth and glossy (waxy).

*Rate of opening.*—Slowly, and in layers, closing at night; fully open in 2–3 weeks.

*Involucral bracts.*—Color. — Outermost involucral bracts are R.H.S. 167 D (greyed-purple group). Aspect. — Thin, dry, membranous.

The Inflorescence:

*Form.*—Flower head is discoid and solitary; usually 1 or 2 buds at the next leaf axis below.

*Flower head size.*—Diameter. — 58 mm. Disc floret portion diameter: 24–25 mm.

*Shape of the flower head.*—Circular; involucral bracts are numerous and imbricate.

*Appearance of the flower head.*—Showy.

*Involucral bracts.*—Form. — Involucral bracts are imbricate in many rows. Involucral bracts are scarious and membranous, but are brightly colored. The involucral bracts are deltoid, enlarged and petal-like. Color. — The margins and tips of the bracts on the upperside of the flower head are as dark as R.H.S. 59 C (red-purple group). Coloring of bracts on the upperside of the flower gives the flower an overall appearance of R.H.S. 58 D (red-purple group) at maturity. Size and number. — Involucral bracts range from 10 mm to 20 mm long and 3 mm to 10 mm wide, and there can be as many as 100 involucral bracts on a flower head.

*Disc florets.*—Form. — Florets are all small, bisexual and tubular. The corolla of the florets is usually 5-lobed. Corolla is usually 7–9 mm long and glaucous (waxy). The upper 3.5 mm of the corolla is usually brightly colored, R.H.S. 24 A (orange group). Androecium. — There are usually 5 stamens borne on the corolla tube. The stamens, including the anthers, are usually united into a tube around the style and become highly reflexed from the point of separation. The stamens protrude from the corolla. Pollen occurs on the adaxial surface of the anthers. Gynoecium. — One pistil per disc floret. The ovary is inferior, and approximately 2 mm tall. The style is often branched. The style protrudes from the corolla about 2 to 3 mm. There is a pappus with many bristles. The bristles are approximately 8 mm long. Color of the bristles is R.H.S. 10 D (yellow group).

*Fragrance.*—None.

*Achenes.*—The achenes rarely germinate.

I claim:

1. A new and distinct variety of *Helichrysum* plant, as illustrated and described.

* * * * *